US006969498B1

(12) United States Patent
Riley

(10) Patent No.: US 6,969,498 B1
(45) Date of Patent: Nov. 29, 2005

(54) SURGICAL INSTRUMENT BRACKET ASSEMBLY

(75) Inventor: Edward D. Riley, Falmouth, ME (US)

(73) Assignee: Riley Medical, Inc., Auburn, ME (US)

( * ) Notice: Subject to any disclaimer, the term of this patent is extended or adjusted under 35 U.S.C. 154(b) by 0 days.

(21) Appl. No.: 10/840,805

(22) Filed: May 7, 2004

(51) Int. Cl.[7] .............................................. A61L 2/00
(52) U.S. Cl. ...................... 422/300; 206/363; 206/369; 206/370; 248/71; 248/188.8; 248/346.03
(58) Field of Search ................................ 422/300, 363, 422/369, 370; 206/336, 369, 370, 363; 248/68.1, 248/71, 73, 220.41, 231.9, 346.03, 346.04, 248/188.8, 188.9, 200, 300

(56) References Cited

U.S. PATENT DOCUMENTS

| 5,424,048 | A |   | 6/1995  | Riley          |         |
|-----------|---|---|---------|----------------|---------|
| 5,681,539 | A | * | 10/1997 | Riley          | 422/300 |
| 5,759,502 | A | * | 6/1998  | Spencer et al. | 422/300 |
| 6,193,932 | B1| * | 2/2001  | Wu et al.      | 422/28  |
| 6,331,280 | B1| * | 12/2001 | Wood           | 422/300 |
| 6,436,357 | B1| * | 8/2002  | Frieze et al.  | 422/300 |

* cited by examiner

Primary Examiner—John Kim
Assistant Examiner—Brad Chin
(74) Attorney, Agent, or Firm—Cesari and McKenna, LLP; John F. McKenna

(57) ABSTRACT

A bracket assembly for supporting medical instruments and the like. The assembly includes a support member formed with lines of vent holes, the vent holes in each line being spaced apart a selected distance. The bracket includes a base strip having a plurality of feet extending down for the base strip, the feet having footprints larger than those of the vent holes and being spaced apart along the base strip a distance substantially equal to an intregal multiple of the selected distance. This allows the bracket to be aligned with a line of vent holes in the support member so that its feet overlie selected ones of the vent holes in that line. A plurality of anchors is provided for anchoring the plurality of feet to the support member at the selected vent holes so that any segment of the base strip between the feet is spaced above the support member so as not to obstruct any underlying vent holes in the support member.

9 Claims, 1 Drawing Sheet

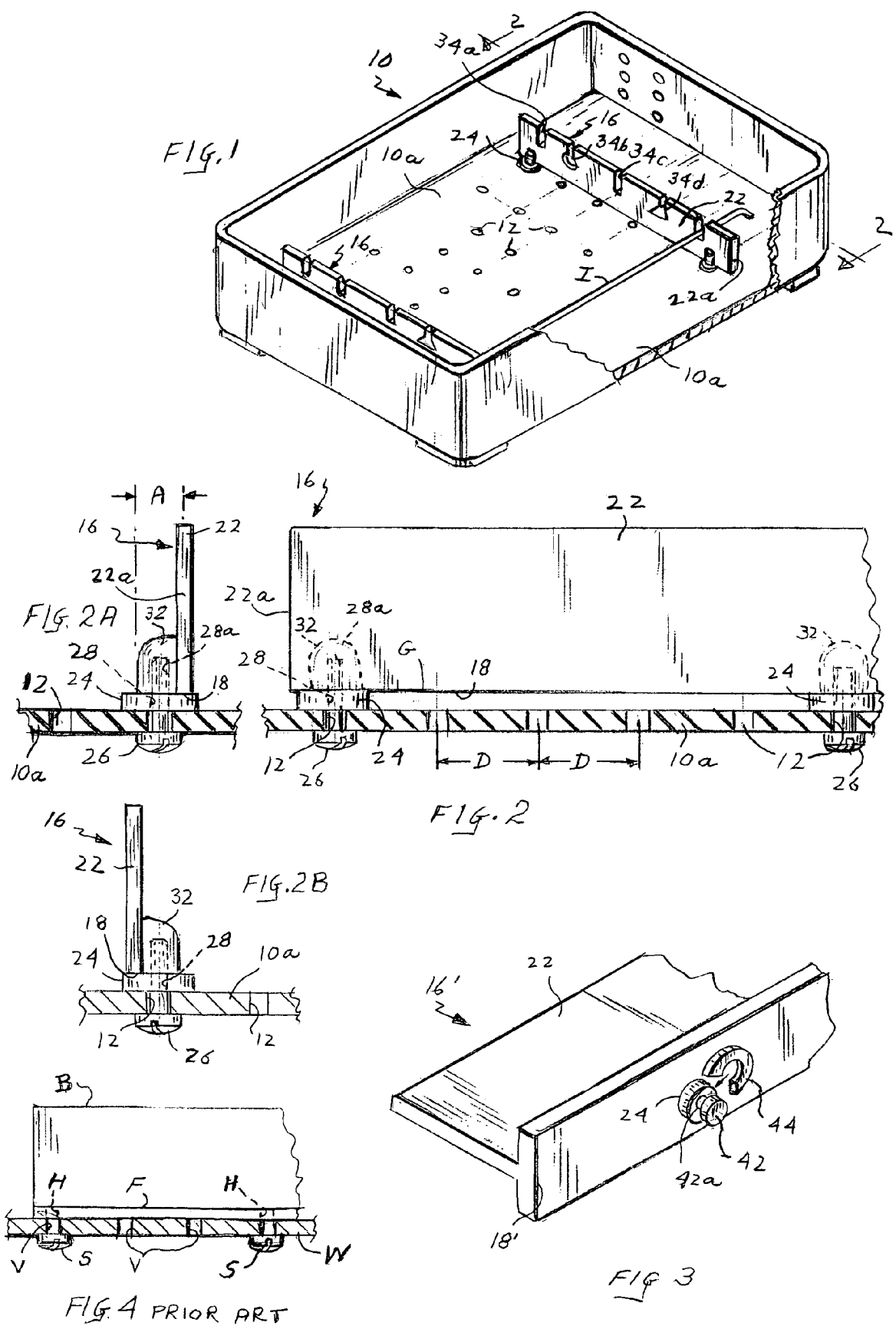

SURGICAL INSTRUMENT BRACKET ASSEMBLY

BACKGROUND OF THE INVENTION

1. Field of the Invention

This invention relates to a surgical instrument retention bracket assembly. It relates particularly to a bracket capable of holding irregularly shaped surgical instruments at fixed positions in a tray or other container.

2. Background Information

There exists in the prior art various retaining means for fixing the positions of articles of one kind or another. These include hooks, pegs, clips, brackets, etc. Such retention means may be used in a wide variety of different applications. They are commonly used in the medical field to fix the positions of various articles such as surgical instruments while those articles are being transported and processed in one way or another. Accordingly, we will describe the invention in that context. It should be understood, however, that the present invention has application in other fields besides the medical field.

Surgical instruments are often transported in trays. Prior to use, the instruments are placed in the tray and subjected to sterilization. In order to maintain a separation between the various instruments in the tray, they are supported or retained by brackets positioned in the tray. Following sterilization, the tray full of instruments may be transported to an operating room and placed close to the surgical team whose members may withdraw in the instruments from the tray as needed for the particular surgical procedure being performed. Usually, the instruments are selectively arranged in the tray so that the instruments can be picked from the tray in the order in which they are needed for the particular procedure. An example of such a tray is disclosed in my U.S. Pat. No. 5,681,539.

As seen from that patent, the known retention means for fixating instruments in a tray include brackets each comprising a relatively long blade having a bottom flange which is releasably secured to the bottom wall of the tray at a selected location thereat. The bracket blade usually has slots, openings, fingers, etc. which are adapted to receive surgical instruments so that the bracket can engage and support the instruments. As shown there, the flange of each bracket rests on the bottom wall of the tray which is invariably formed with a multiplicity of vent holes to allow steam to circulate through the tray during the sterilization process. The brackets are adjustably anchored to the bottom wall by utilizing selected vent holes. In other words, flanges are formed with fastening means which may be aligned with selected vent holes in the bottom wall of the tray. This allows complementary fastening means to be installed from the underside of the tray to secure the flange to the bottom wall at those selected vent holes.

The fastening means on the flange may simply be holes for receiving threaded fasteners inserted through the selected vent holes in the bottom wall of the tray. Alternatively, the fastening means on the flange may be small diameter cylindrical posts having reduced diameter necks, the posts being dimensioned and arranged along the flange so that they can be received in the selected vent holes and releasably anchored to the bottom wall of the tray, e.g., by engaging C-clips around the post necks that project below the tray bottom wall. By positioning pairs of brackets appropriately in the tray, the brackets can engage and support the opposite ends of different length medical instruments.

While such brackets are satisfactory for many applications, we have found that when a conventional bracket is installed as aforesaid in an instrument tray, the bracket blocks all of the underlying vent holes in the tray bottom wall thereby preventing the circulation of steam through all of those holes. This is illustrated in FIG. 4 which shows a conventional bracket B resting on a tray bottom wall W formed with a rectangular array of vent holes V. Bracket B is anchored to wall W by screws S inserted through selected vent holes V and threaded into anchoring holes H in the flange F at the bottom of the bracket. As seen from FIG. 4, flange F covers all of the vent holes V under the bracket and thereby prevents steam from entering or leaving the tray through those holes. Since a given tray may be fitted with many such brackets B, the presence of those brackets can materially reduce the circulation of a sterilizing fluid through the tray. This, in turn, materially increases the length of time it takes to properly sterilize the medical instruments supported in the tray by the brackets.

The prior brackets are also disadvantaged in that the anchoring holes H in the underside of the bracket B are formed by a drilling operation. This extra step in the manufacturing of the bracket adds to the cost thereof and constitutes a negative factor in the overall sales of the product.

SUMMARY OF THE INVENTION

Accordingly, the present invention aims to provide a bracket assembly for releasably supporting a medical instrument or other article in a perforated tray or container.

A further object of the invention is to provide a bracket assembly of this type which does not interfere with the circulation of sterilization fluid through the tray or container.

Another object of the invention is to provide an improved bracket for releasably retaining a medical instrument or other article in a sterilization tray or container, yet which permits quick release of the instrument or article when necessary.

Another object of the invention is to provide such a bracket which is relatively easy and inexpensive to manufacture in quantity.

Other objects will, in part, be obvious and will, in part, appear hereinafter. The invention accordingly comprises the features of construction, combination of elements and arrangement of parts which will be exemplified in the following detailed description and the scope of the invention will be indicated in the claims.

Briefly, my bracket assembly comprises a bracket adjustably mounted to a perforated support member which may be the bottom wall of a sterilization tray or other container formed with a multiplicity of vent holes arranged in lines, e.g. a grid. The bracket includes a base strip which supports an upstanding blade which may be formed along its length with cut-outs, slits and the like shaped and arranged to receive medical instruments of different sizes and shapes. Formed integrally with the base strip is a lengthwise series of feet which extend below the base strip and have a footprint which is larger than that of the vent holes in the support member.

In accordance with the invention, the depending feet of each bracket are spaced apart a distance which is an integral multiple of the centerline distance between adjacent vent holes in the support member. In other words, the bracket may be positioned on the support member so that it is aligned with a given line of vent holes and so that the bracket feet are positioned above selected vent holes in that line. The bracket may then be releasably anchored to the support member by fastening means engageable to the feet from the underside of the support member at those selected vent holes. When the bracket is so anchored to the support member, the segment or segments of the base strip between the feet are spaced from the support member so that the vent holes below those segments are not occluded by the base strip. Resultantly, steam or other fluid is free to circulate through those unobstructed vent holes in the support member.

Preferably, the series of feet depending from the base strip is offset to one side of the longitudinal centerline of the base strip. This enables the bracket to be anchored to a selected line of vent holes in the support member in two different orientations, 180° apart. Resultantly, the blade component of the bracket may be located at two different positions on the support member offset in a direction perpendicular to that line of vent holes. In other words, the positions or spacing of the brackets along the support member can be fine tuned to accommodate the instrument or instruments supported by the brackets, e.g. to avoid protuberances on the instrument(s).

A single bracket may be used to retain relatively short instruments or other articles. The retention of longer or larger instruments or articles may require that two or more brackets be spaced parallel to one another on the support member so that the brackets can support opposite ends of, or different portions of, those instruments or articles, the bracket spacing(s) or position(s) being determined by the lengths or sizes of the instruments or articles.

The bracket component of the assembly may be a simple molded plastic part that can be made in quantity at relatively low cost. Therefore, the bracket assembly as a whole is relatively economical to make and should find wide application particularly in the medical industry where the retention of instruments and other articles in a container or the like is of some importance.

BRIEF DESCRIPTION OF THE DRAWINGS

For a fuller understanding of the nature and objects of the invention, reference should be made to the following detailed description taken in connection with the accompanying drawings, in which:

FIG. 1 is a perspective view with parts broken away of a bracket assembly for retaining surgical instruments or the like incorporating the invention;

FIG. 2 is a sectional view on a larger scale taken along line 2—2 of FIG. 1;

FIG. 2A is an end view showing the bracket of FIG. 2 in a first orientation;

FIG. 2B is a similar view showing the bracket in a second orientation;

FIG. 3 is a fragmentary perspective view from below showing a second bracket embodiment for use in the FIG. 1 assembly, and FIG. 4, already described, is a view similar to FIG. 2 showing a conventional bracket for supporting medical instruments.

DESCRIPTION OF THE PREFERRED EMBODIMENTS

Refer to FIG. 1 of the drawings which illustrates a generally rectangular medical tray 10 having a bottom wall 10a containing a rectangular array of small vent holes 12. Positioned in tray 10 is a pair of spaced-apart brackets shown generally at 16 which are releasably anchored to bottom wall 10a by anchoring means to be described later. The brackets 16 are spaced parallel to one another in the tray and are arranged to support and fixate one or more instruments I in the tray and to readily release the instrument(s) when needed by a surgeon or other person.

Referring now to FIGS. 2 and 2A, each bracket 16 is a unitary article which may be made of a suitable rigid metal or plastic material. Preferably, the bracket is molded of a suitable plastic material such as polyetherimide or polyphenylsulfone so that it is able to withstand sterilization temperatures and can be made in quantity relatively inexpensively using conventional molding processes.

Bracket 16 comprises a generally rectangular base strip 18 which, in the illustrated embodiment, is constituted by the lower edge or surface of an upstanding blade 22. Extending down from base strip 18 is a linear series of equally spaced apart feet 24, each of which preferably extends laterally beyond opposite sides of base strip 18. The feet 24 should have a footprint which is larger than that of the vent holes 12 in tray 10 and the feet should be spaced apart along the base strip 18 a distance which is an integral multiple of the centerline distance D between adjacent vent holes 12 in the columns and rows of such holes in the bottom wall 10a of tray 10. This enables each bracket 16 to be positioned on the tray bottom wall 10a so that its feet 24 are aligned with selected vent holes 12 in a given row (or column) of vent holes in wall 10a.

Thus, in the bracket embodiment depicted in FIG. 2, feet 24 are spaced apart a distance corresponding to the distance between the first, sixth eleventh, etc. vent holes 12. Resultantly, when the bracket 16 is resting on wall 10a with feet 22 in alignment with holes 12, the segment(s) of the base strip 18 between adjacent feet 24 is spaced above wall 10a so that a gap G exists between base strip 18 and the underlying vent holes 12 between adjacent feet 12 so that the bracket does not occlude those vent holes.

In order to releasably anchor bracket 16 to the tray bottom wall 12a, threaded fasteners 26 may be inserted through the vent holes 12 underlying feet 24 and threaded into holes 28 formed in those feet.

As best seen in FIGS. 2A and 2B, preferably the series of feet 24 of each bracket 16 is offset to one side of the longitudinal centerline of base strip 18 so that the holes 28 formed therein are offset laterally relative to the bracket blade 22. Resultantly, when a bracket 16 is mounted in tray 10 so that its blade end 22a faces to the left as shown in FIG. 2, that bracket will be located at a selected location along the long dimension of the tray. On the other hand, when that same bracket is rotated 180° so that the blade end 22a faces toward the right, due to the aforementioned lateral offset, that bracket 16 will be shifted along tray 10, i.e. perpendicular to the longitudinal axis of the blade, a distance A as shown by a comparison of FIGS. 2A and 2B. This allows a fine adjustment of the bracket locations in tray 10 to accommodate the various medical instruments I to be supported by the brackets. For example, it may allow various projections on the instruments to be avoided when seating the instruments on the brackets.

As best seen in FIGS. 2, 2A and 2B, in order that a threaded fastener hole 28 may be molded into bracket 16 at the time of manufacture, the bracket may be provided with an integral nose 32 which extends above each foot 24 adjacent to blade 22. In that event, the hole 28 in each foot 24 may have an extension 28a which extends into the corresponding nose 32 and is threaded to receive a fastener 26.

As shown in FIGS. 1 and 2, the blades 22 of the brackets may be formed with various slits, slots or cutouts 34a to 34d shaped and sized to receive and retain various different medical instruments I as is well known in the art.

Refer now to FIG. 3 which shows another bracket embodiment 16'. In this case, the bracket base strip is constituted by a flange 18' extending along the lower edge of the bracket blade 22'. Bracket feet 24' extend down from the underside of flange 18'. As described above in connection with FIG. 2, the feet 24' have footprints which are larger than those of the vent holes 12 in tray 10 and they are spaced apart a distance corresponding to an integral multiple of the vent hole spacing in a given column or row of the hole array in the bottom wall of tray 10 in FIG. 1.

Instead of using threaded fasteners to anchor bracket 16' to the tray wall 10a, in this embodiment, each foot 24' is formed with a depending cylindrical post 42 having a reduced diameter neck 42a. These posts are dimensioned and disposed along the flange 18' so that they can be received in selected holes 12 in a given column or row of holes in the tray bottom wall 10a depicted in FIG. 1. The posts may be shaped and arranged to snap into the holes 12 or they may be releasably anchored to the tray bottom wall 10a by engaging a conventional C-clip 44 around the post necks 42a that project below the tray bottom wall 10a.

As described above, the brackets 16 and 16' may be made quite easily using conventional molding materials and techniques. Therefore, they should find wide application, particularly in the medical field.

It will thus be seen that the objects set forth above among those made apparent from the preceding description, are efficiently attained. Also, certain changes may be made in the above construction without departing from the scope of the invention. For example, the fasteners 26 may be expandable or friction fasteners, rivets etc. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A bracket assembly for supporting medical instruments, said assembly comprising
   a support member formed with lines of vent holes, the vent holes in each line being spaced apart a selected distance;
   a bracket including a base strip having a longitudinal centerline and a plurality of feet depending from the base strip so that said feet extend appreciably below all segments of the base strip, said feet each having a footprint larger than that of each of said vent holes and being spaced apart along the base strip a distance substantially equal to an integral multiple of said selected distance so that said bracket may be aligned with a line of vent holes in the support member so that said feet overlie selected ones of the vent holes in that line, and
   a corresponding plurality of anchors for anchoring said plurality of feet to the support member at said selected vent holes whereby all segments of the base strip are spaced above the support member so as not to obstruct any underlying vent holes in the support member.

2. The bracket assembly defined in claim 1 wherein the support member comprises a sterilization tray bottom wall.

3. The bracket assembly defined in claim 1 wherein the bracket includes a blade extending from the base strip in the opposite direction from said feet.

4. The bracket assembly defined in claim 3 wherein the bracket comprises a unitary part molded of a plastic material able to withstand sterilization.

5. The bracket assembly defined in claim 1 wherein the plurality of anchors is offset to one side of said longitudinal centerline of the base strip.

6. The bracket assembly defined in claim 1 wherein each of the plurality of anchors includes
   a fastening hole in the corresponding foot, and
   a fastener extending through the selected vent hole underlying that foot into said fastening hole in that foot.

7. The bracket assembly defined in claim 1 wherein each of the plurality of anchors includes
   a post having an end and extending down from the corresponding foot into the selected vent hole underlying that foot, and
   means for securing said post in said selected underlying vent hole.

8. The bracket assembly defined in claim 7 wherein the securing means comprise an enlargement on said end of said post and which engages under an edge of said selected underlying vent hole.

9. The bracket assembly defined in claim 8 and further including a clip engageable around said post between said enlargement and the support member.

* * * * *